(12) United States Patent
Harrel

(10) Patent No.: US 8,096,944 B2
(45) Date of Patent: Jan. 17, 2012

(54) AIR SHIELD FOR VIDEOSCOPE IMAGERS

(76) Inventor: Stephen K. Harrel, Dallas, TX (US)

( * ) Notice: Subject to any disclaimer, the term of this patent is extended or adjusted under 35 U.S.C. 154(b) by 1076 days.

(21) Appl. No.: 11/977,960

(22) Filed: Oct. 26, 2007

(65) Prior Publication Data
US 2009/0112065 A1 Apr. 30, 2009

(51) Int. Cl.
A61B 1/12 (2006.01)

(52) U.S. Cl. ......... 600/157; 600/133; 600/158; 600/169

(58) Field of Classification Search ........... 600/157–159
See application file for complete search history.

(56) References Cited

U.S. PATENT DOCUMENTS

| | | | |
|---|---|---|---|
| 4,497,550 A * | 2/1985 | Ouchi et al. | 359/509 |
| 4,790,751 A | 12/1988 | Reinhardt et al. | |
| 5,230,621 A | 7/1993 | Jacoby | |
| 5,313,934 A | 5/1994 | Wiita | |
| 5,339,800 A * | 8/1994 | Wiita et al. | 600/109 |
| 5,400,767 A * | 3/1995 | Murdoch | 600/157 |
| 5,429,502 A | 7/1995 | Cooper et al. | |
| 5,464,008 A * | 11/1995 | Kim | 600/157 |
| 5,569,161 A | 10/1996 | Ebling et al. | |
| 5,575,756 A * | 11/1996 | Karasawa et al. | 600/157 |
| 5,637,075 A * | 6/1997 | Kikawada | 600/153 |
| 5,697,888 A | 12/1997 | Kobayashi | |
| 5,919,158 A | 7/1999 | Saperstein et al. | |
| 5,944,654 A * | 8/1999 | Crawford | 600/157 |
| 6,007,333 A | 12/1999 | Callan et al. | |
| 6,500,114 B1 | 12/2002 | Petitto et al. | |
| 6,699,185 B2 * | 3/2004 | Gminder et al. | 600/157 |
| 6,873,409 B1 * | 3/2005 | Slater | 356/301 |
| 7,226,451 B2 | 6/2007 | Shluzas et al. | |
| 7,233,820 B2 | 6/2007 | Gilboa | |
| 7,341,556 B2 * | 3/2008 | Shalman | 600/157 |
| 7,726,821 B2 * | 6/2010 | Bral | 359/511 |
| 2006/0020165 A1 | 1/2006 | Adams | |
| 2006/0200001 A1 | 9/2006 | Keller | |
| 2008/0319266 A1 | 12/2008 | Poll et al. | |

OTHER PUBLICATIONS

Fiberoptic Aspirators Surgical, Quality Aspirators Product Catalog, pp. 5-8.
Micro Fiber Optics, Endodontic Aspirators, Salvin 2007 Product Catalog, p. 107.

* cited by examiner

Primary Examiner — Matthew J Kasztejna
(74) Attorney, Agent, or Firm — Roger N. Chauza, PC

(57) ABSTRACT

An air shield for a videoscope imager to prevent obscuring of the optical input by body liquids and tissue particles. The imager is extended through a tube carrying a pressurized gas so that when the gas escapes from the end of the tube, it generates an air stream envelope around the optical input of the imager and prevents liquids and particles directed toward the optical input from contacting the optical input. The pressurized gas flows continuously during the medical or dental procedure to maintain a constant resistance to liquids and matter directed to the optical input of the imager.

19 Claims, 6 Drawing Sheets

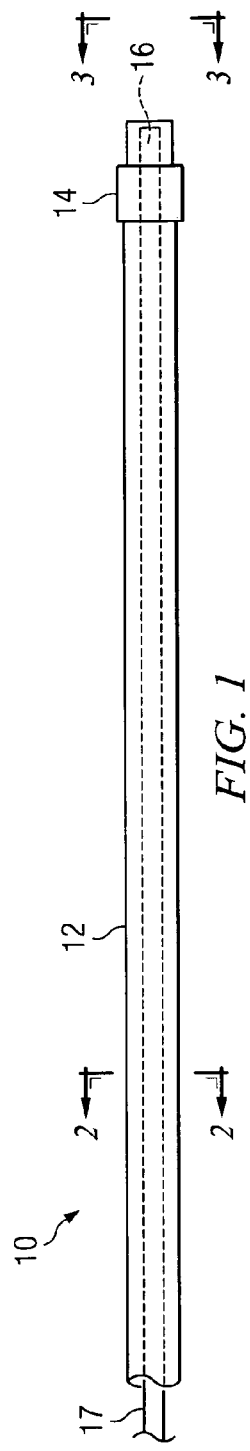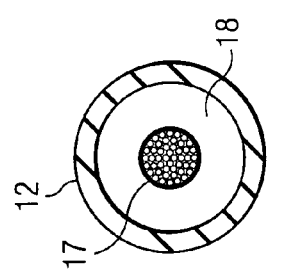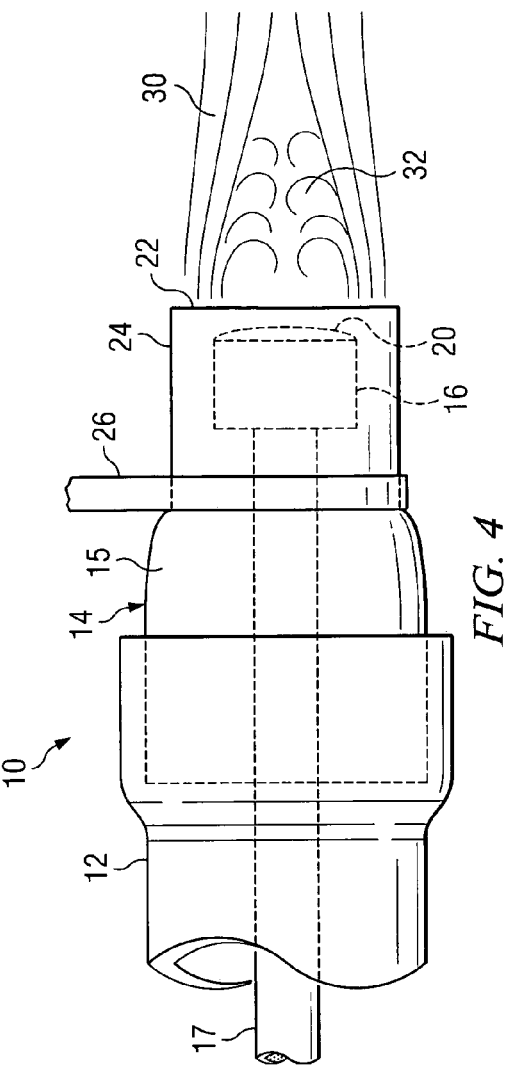

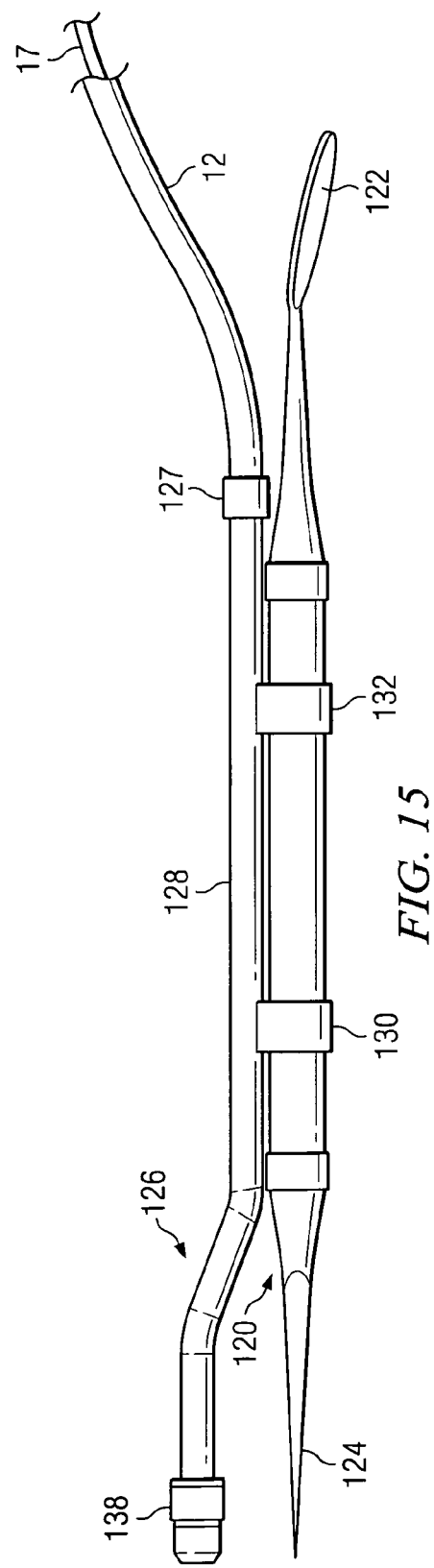

AIR SHIELD FOR VIDEOSCOPE IMAGERS

TECHNICAL FIELD OF THE INVENTION

The present invention relates in general to imaging apparatus for use with endoscopic and videoscope equipment, and in particular relates to methods and apparatus for maintaining imaging lenses clean during minimally invasive surgical procedures.

BACKGROUND OF THE INVENTION

Significant advances have been made in the medical and dental fields to better enable doctors to view and observe the treatment area during surgical procedures in the medical and dental field. Where previously a doctor used a head-mounted magnifying eyepiece to view the tissue area, now doctors routinely use electronic imaging apparatus to display an enlargement of the tissue area so that the area can be viewed on a screen with selected angles, intensities, colors, and so that a number of persons can simultaneously view the same tissue area of interest. Moreover, with electronic imaging, the images can be magnified for viewing, stored for archive purposes, and can be viewed at remote locations by students and other interested parties.

Endoscopes of various types using imaging equipment, namely videoscopes, include imaging apparatus for viewing tissue areas during traditional invasive and minimally invasive procedures. Videoscopes typically include a camera at the end of a flexible member, as well as electronic image gathering equipment located near the instrument. The entire end of the flexible member is manipulated by the doctor so that the instrument end of the videoscope can be controlled by the doctor to carry out the desired medical or dental procedure. When carrying out an invasive procedure, the end of the videoscope is inserted through an incision in the patient's skin and guided by the doctor to the tissue site of interest. The imaging apparatus is often a miniature camera or a bundle of optical fibers which carry the composite image of the tissue site to image processing and display equipment located in view of the doctor. The videoscope also includes an image input device and a light producing mechanism to cast a beam of light on the area of the surgical procedure. By manipulating the end of the videoscope in or around the patient's tissue, the doctor can view the procedure on the video display, which might otherwise be very difficult or impossible for the doctor to see with the naked eye or head-mounted optical magnifying equipment.

In the periodontal area of practice, videoscopes are often employed to observe the gingival pocket or sulcus where granulation tissue is removed from the bone, or where plaque dental calculus is removed from the root cementum. The dental tool is inserted into the gingival pocket and manipulated by the doctor to carry out the procedure. At the same time, the doctor or an assistant will insert a water tube device and endoscope imager to lavage the area, and also to capture the area of operation so that it can be automatically enlarged and displayed to the doctor to facilitate the accuracy of use of the dental tool for removal of the undesired tissue without damaging the surrounding tissue. A liquid can be used to cleanse the lens of the imager so that a clear line of sight is maintained to the area of the procedure.

A problem often encountered with the use of an imaging type of endoscope or a videoscope is that of maintaining the lens or optical input of the imager clean during the procedure. It can be appreciated that when the optical input of the imager is embedded in fluids or becomes covered either partially or fully with blood or other body fluids, the image to be collected is often not discernable. The debris on the lens can cloud or fully obscure the tissue, whereupon the procedure must be temporarily discontinued until the lens is cleaned. Sometimes, the videoscope must be withdrawn from the patient before it can be manually cleaned.

In many surgical operations, the area of the procedure must be lavaged with a stream of water to clean the same. The flushing of the area often causes the debris to be splattered onto the lens of the imager, thus requiring the same to be removed and cleaned, or withdrawn somewhat during the lavage procedure. It can also be appreciated that even when water or another clear liquid is used to keep the lens clean, the cleaning liquid can often leave droplets on the lens, thereby creating inaccurate capturing of the image. In addition, in cases where the imager is immersed within the liquid during the operation, the motion and turbulence of the liquid produces inaccurate and distorted images.

In minimally invasive periodontal surgery, the surgical area is constantly bathed in a mixture of saliva and blood. When a conventional video imager is used, whether it be a miniature camera or the end of a fiber optic bundle, the optical input quickly becomes contaminated with blood and must be repeatedly cleaned. If a rotary or ultrasonic instrument is used, of the type that produces copious spray and blood-contaminated aerosols, the image captured becomes virtually unusable. This is also the case in many medical procedures that are "open" such as plastic surgery, tissue removal from the skin, etc. The image contamination problem is minimized in closed surgical procedures, such as abdominal surgery, by introducing a second or third tube that fills the abdomen with an inert gas (usually nitrogen), and also possibly a suction tube. The end of the videoscope nevertheless becomes contaminated and must be frequently removed and cleaned.

The cleaning of the imager at the end of an videoscope can often be accomplished by flooding the area with water or other clear liquid in order to rinse the residue off the lens. This is accomplished by providing a lumen in the flexible member of the videoscope to carry pressurized water from a reservoir to the end of the videoscope. Such videoscopes are described in U.S. Pat. No. 5,230,621 by Jacoby and U.S. Pat. No. 6,007,333 by Calan et al. These videoscopes are believed to function well for their intended purpose, but the excess liquid must be evacuated from the surgical site, or it will also obscure and interfere with the line of sight to the area of interest. In addition, a clean source of water must be available, as well as a system to pressurize the water or other clear cleaning liquid that is utilized. The videoscopes described in the prior art facilitate the removal of splatter once it accumulates on the lens of the imager by flooding the area adjacent the lens with water, but do not address prevention of the same.

From the foregoing, it can be seen that a need exists for a technique to employ a videoscope and prevent the lens of the imager from coming into contact with obscuring films and splatter, thus maintaining the lens clean without having to use a cleansing liquid or to purposefully clean the lens intermittently to maintain a clear line of sight to the tissue of interest. Another need exists for a videoscope that can be conveniently attached to a hand-held instrument. Another need exists for a videoscope that is particularly, but not exclusively, well adapted for surgical procedures including periodontal, plastic and facial procedures.

SUMMARY OF THE INVENTION

In accordance with the principles and concepts of the invention, there is disclosed a videoscope with an imager having an optical input embedded within the envelope of an air stream to thereby deflect particles directed toward the lens. An object of the invention is to prevent debris from contaminating the optical input of the imager so that cleaning thereof is either substantially reduced or eliminated.

In accordance with one embodiment of the invention, disclosed is a method of maintaining the imager of a videoscope clear of debris that can otherwise obscure the optical input thereof. The method includes embedding the optical input of the imager in an envelope of a stream of gas, and directing the gas stream away from the optical input so that the debris initially directed toward the optical input is redirected by the gas stream. The spent gas is then allowed to escape to the atmosphere.

In accordance with another embodiment of the invention, disclosed is a method of maintaining the imager of a videoscope clear of debris that can otherwise obscure an optical input of the imager, where the method includes the steps of passing a gas away from the optical input of the imager to form an envelope of gas that encloses the optical input, and to form an inner volume of the envelope of gas characterized by a turbulent flow that is adapted for removing droplets of liquid from the optical input. The debris initially directed toward the optical input is redirected away from the optical input using the force of the gas. The gas is then allowed to escape to the atmosphere.

In accordance with yet another embodiment of the invention, disclosed is a gas shield for maintaining the imager of an videoscope clear of debris that can otherwise obscure an optical input of the imager. The gas shield includes a tubular member for carrying a pressurized gas, where the tubular member has a first end receiving pressurized gas from a source, and a second end. At least one conductor carries signals representative of an image captured by the imager, the conductor extends through the tubular member to the imager. The optical input of the imager is located adjacent the second end of the tubular member so that the pressurized gas carried by the tubular member passes over the optical input of the fiber optic conductor and generates an envelope of a gas stream around the optical input to thereby redirect the debris away from the optical input of said imager.

BRIEF DESCRIPTION OF THE DRAWINGS

Further features and advantages will become apparent from the following and more particular description of the preferred and other embodiments of the invention, as illustrated in the accompanying drawings in which like reference characters generally refer to the same parts, functions or elements throughout the views, and in which:

FIG. 1 is a side view of a portion of the imager comprising a miniature camera within a tube of pressurized air;

FIG. 2 is an enlarged cross-sectional view of the air shield, taken along line 2-2 of FIG. 1;

FIG. 3 is an enlarged end view of the air shield, taken along the line 3-3 of FIG. 1;

FIG. 4 is an enlarged side view of the end of the air shield showing the envelope of the air stream in which the lens of the imager is embedded;

FIG. 15 is a side view of another instrument to which the air shield of the invention can be attached.

DETAILED DESCRIPTION OF THE INVENTION

Figure 5:
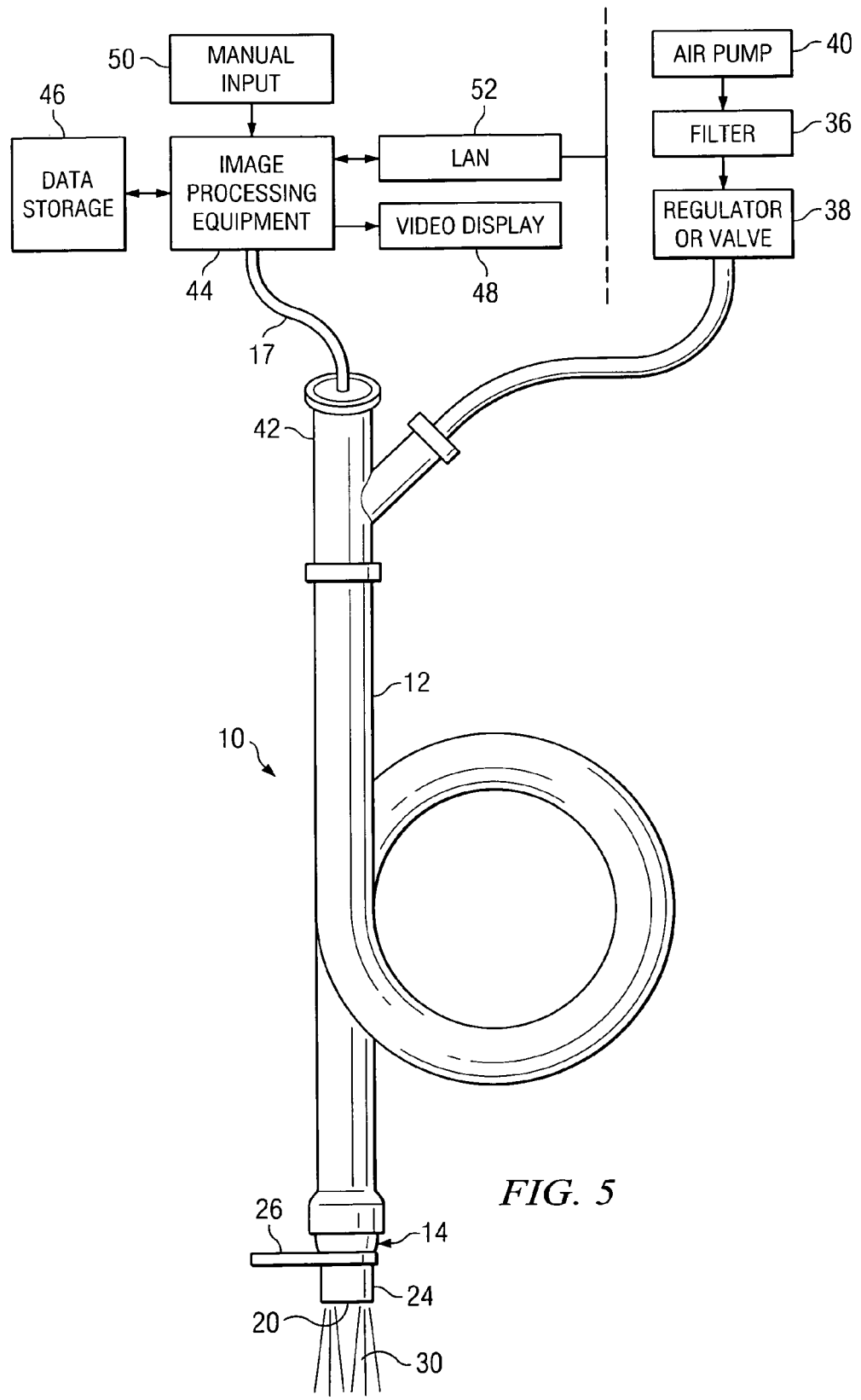
FIG. 5 is a diagram of a system in which the invention can be advantageously practiced.

With reference to FIG. 1, there is shown the air shield 10 according to one embodiment of the invention. The air shield 10 includes a flexible plastic, rubber or silicon tube 12 having a termination fitting 14 comprising a tubular metal member fixed to the end of the tube 12. While not shown, the other end of the tubing 12 is connected to a source of pressurized gas, such as air, nitrogen or other suitable gas medium. Inserted within the tubing 12 is a miniature camera 16 with a lens comprising the image input of the imager. In the preferred embodiment of the invention, the miniature camera 16 has a 3.5 megapixel semiconductor imager, is self focusing, has a diameter of about 2.8 mm, and is obtainable from Olympus as model number ENF-V2. The miniature camera 16 couples digital signals representative of the image captured, through an electrical cable 17 to remotely located image processing equipment. The camera 16 includes a lens (not shown) which is positioned near the end of the tube termination fitting 14. Conventional endoscope-type optical imagers using optical fiber bundles as image inputs can be used with equal effectiveness. The other end of the electrical cable 17 carrying digital signals output from the camera 16 is connected to imaging apparatus for processing the digital image signals and presenting the same on a video monitor or screen for display. The video camera 16 is also equipped with one or more light emitting devices to illuminate the area to be imaged. Signals driving the illumination devices are carried by conductors in the electrical cable 17.

The air shield 10 is effective to produce a protective airstream envelope all around the lens of the imager and prevent particles of liquid and other debris from reaching the lens. Thus, the surgical procedure can be carried out with less concern of keeping the lens clean. Indeed, with the air shield 10 of the invention, the imager can be located closer to the area of interest than would otherwise be possible, whereby the surgeon can better observe the procedure and not be interrupted by lens cleaning procedures. This alleviates the concerns heretofore encountered, as the doctor or attendant needed to be aware of where to place the imager so as not to be in an area likely to be splattered with tissue particles or body liquids. In many instances, the location where the imager is best focused on the area of interest, is the same location where tissue particles and body fluids are directed. It is appreciated that when the camera 16 is moved closer to the object to be observed, the image is effectively magnified and made larger on the visual display. Irrespective of the position of the camera 16 with respect to the object to be observed, the camera 16 of the preferred embodiment is self focusing.

FIG. 2 is a cross-sectional view of the air shield 10 showing the flexible air tube 12 with the camera 16 and electrical conductor 17 inserted therethrough, and the annular-shaped air conduit 18 encircling the electrical cable 17. The electrical cable 17 need not be centered within the air tube 12, but the inside diameter of the air tube 12 must be greater than the outside diameter of the camera 16. The insertion of both the cable 17 and the camera 16 within the air tube 12 provides a composite tubular member which provides two functions. First, the imager collects light signals so that the same can be viewed, often after a desired magnification has been selected by the operator. Secondly, the air tube 12 generates the air envelope around the optical input of the imager and prevents debris from contaminating the optical input. Those skilled in the art may find in some situations that the air tube 12 can be provided separate from the camera 16. In this latter case, the air tube 12 could be smaller in diameter, and the end of the air tube 12 can be integrated with the camera 16 to produce the air pressure envelope therearound.

FIG. 3 is an end view of the air shield 10 according to a preferred embodiment of the invention. The metal fitting 14 functions to terminate the end of the air tube 12 and provide an annular orifice 22 around the frontal end of the camera 16. The annular-shaped air conduit 18 of the air tube 12 effectively terminates in the annular orifice 22 of the fitting 14. The fitting 14 also functions to allow anchoring the end of the air tube 12, and thus the lens 20 of the camera 16, to a medical wand or other instrument, such as a hand-held aspiration instrument. The lens 20 of the camera 16 is positioned axially within the fitting 14 to provide an annular orifice 22 for the flow of air exiting the fitting 14. In a preferred embodiment, the camera 16 is constrained from axial movement within the fitting 14 at a remote location, not at the end of the fitting 14. However, the fitting 14 could be structured to prevent the camera 16 from sliding therethrough, and yet allow air flow around the lens 20. Preferably, the camera 16 is inserted into the flexible air tube 12 until the lens 20 protrudes through the end of the fitting 14, and then the camera 16 is slowly withdrawn back into the fitting 14 until the annular edge of the opening in the fitting 14 is barely visible on the video display. In practice, the camera 16 can be somewhat beyond the annular edge of the fitting 14, or somewhat withdrawn in the fitting 14, or anywhere therebetween. Through experimentation, it has been found that the optimum operation of the imager is obtained when the lens 20 is withdrawn in the fitting 14 about 1-3 mm. In surgical environments where there is an extremely heavy presence of body fluids and tissue particles, the camera 16 can be withdrawn further into the end of the fitting 14. The cable 17 of the camera 16 is then clamped to the air tube 12 at the remote end to prevent relative axial movement therebetween.

FIG. 4 illustrates the details of the air shield 10 and the air stream envelope 30 during operation thereof. The fitting 14 includes a body 15 over which the end of the air tube 12 is frictionally attached. The fitting 14 includes a frontal barrel portion 24 with an open end. The opening (FIG. 2) in the end of the barrel 24 is larger than the outside diameter of the camera 16 and the lens 20 to allow the escape of air circumferentially in the orifice 22 encircling the lens 20. The fitting 14 includes a bracket 26 welded thereto for fastening the fitting 14 to a surgical device, such as the suction tube of an aspirator.

According to an important feature of the invention, the pressurized air carried in the annular conduit 18 between the inner sidewall of the air tube 12 and the camera 16 exits the end of the air shield 10 and creates an envelope 30 around the lens 20. The air envelope 30 is directed outwardly from the end of the annular orifice 22 and prevents particles of tissue and body fluids from striking or otherwise contacting the lens 20. Importantly, the air shield 30 does not distort or create disturbances or inaccuracies in the image collected by the lens 20 of the imager. Particles created during the surgical procedure that are directed toward the lens 20 are redirected by the force of the air envelope 30 and carried away from the lens 20. The air envelope 30 is believed to be characterized as having an area of turbulent air flow 32 adjacent the lens 20. In practice, particles of liquid that have gotten on the lens 20 of the camera 16 are soon swept off by the turbulent flow of air 32. Droplets of moisture that may accumulate on the lens 20 can be seen on the video display to be agitated by the turbulent air and eventually be pulled off the lens of the camera 16 and swept away by the outer envelope of the air stream 30. Thus, a suction force appears to exist just in front of the lens of the camera 16 which is effective to pull droplets off the lens 20. The turbulent air flow 32 is completely enclosed within the air envelope 30 and is not accessible unless traversed by the outward force of the air stream exiting the annular orifice 22.

FIG. 5 illustrates a system in which the invention can be advantageously practiced. The system includes the air shield 10 of the invention which incorporates an imager and a continuous air stream 30 for preventing the lens 20 of the imager from becoming contaminated with fluids and particles that would obscure and inhibit capturing accurate and complete images. The air conduit 18 is connected to a source of air or gas via an optional filter 36 and an adjustable regulator or valve 38 to control the volume of air and thus the pressure that continuously passes through the air tube 12. The source of air or gas can be a pump 40 or a tank of pressurized air or gas. The regulator 38 can be of any conventional type that regulates the pressure of the gas within the air tube 12. Alternatively, a manually valve 38 can be employed to control the volume of air that passes into the air tube 12. The optional filter 36 prevents any particles or lubricant from entering the air tube 12. A pressure gauge (not shown) can also be used to determine and set the pressure of the gas within the air conduit 18 of the air tube 12. While not critical to the operation of the air shield 10, the pressure of air that is continuously delivered to the air tube 12 can be within the range of about 3 psi to about 6 psi. Of course, the velocity of air exiting the annular orifice 22 is a function of the annular area of the orifice 22, as well as the pressure of the air within the air tube 12. Again, while not critical to the operation of the air shield 10, the radial dimension of the annular orifice 22 can be between 0.15 mm and 0.35 mm, and preferably about 0.25 mm. The pressure and area parameters can be chosen to achieve the results desired.

The air tube 12 is connected to a flexible rubber or plastic "Y" fitting which includes a branch 42 into which the camera 16 and associated electrical cable 17 are inserted and sealed against air leaking out of the branch 42. The tight friction fit between the fitting 42 and the electrical cable 17 of the camera 16 prevents axial movement therebetween. The electrical cable 17 is coupled to standard image processing equipment 44 to process the image signals as to pixel location and color. Preferably, the image processing equipment 44 is adapted to provide numerous enhancements of the image, such as zooming, rotating, cropping, image capture and store, color, hue, brightness, contrast, etc. The processed signals of the image can be stored in a data base 46, and can be displayed in real time on a video display 48. A manual input 50 is provided so that the surgeon can communicate with the image processing equipment 44. The various enhancements available can be selected by the surgeon by use of the manual input 50, which could be a keyboard or touch screen. As an option, the image processing equipment 44 can be connected to a local area network 52 for remote display of the images captured by the imager of the air shield 10.

Figure 6:
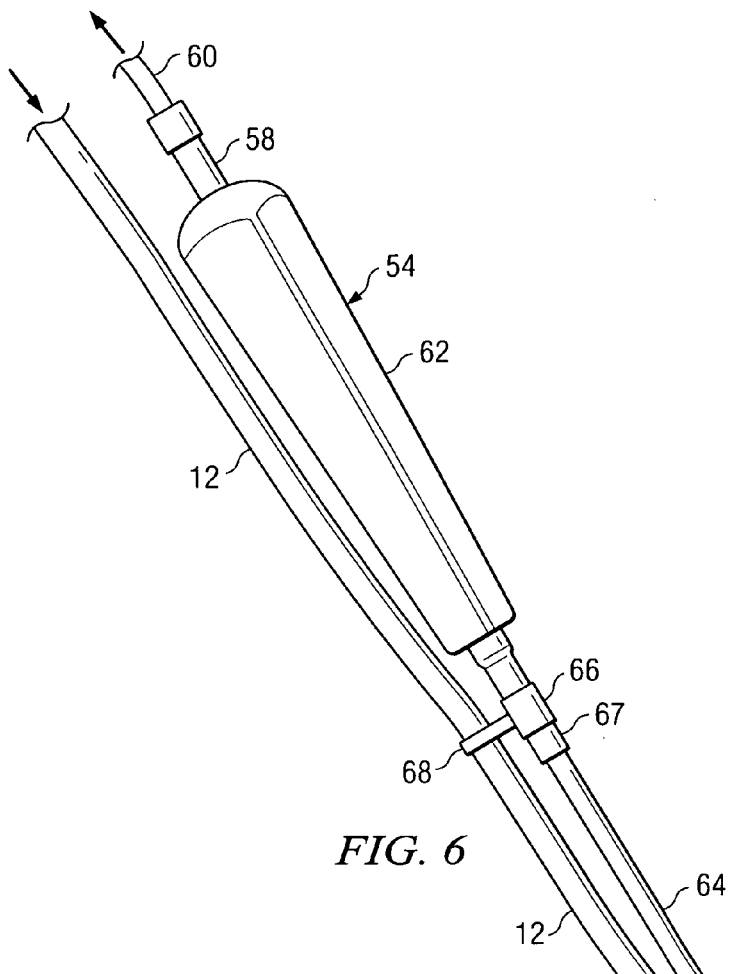
FIG. 6 is illustrates a surgical aspirator to which the air shield of the invention is attached.
Figure 7:
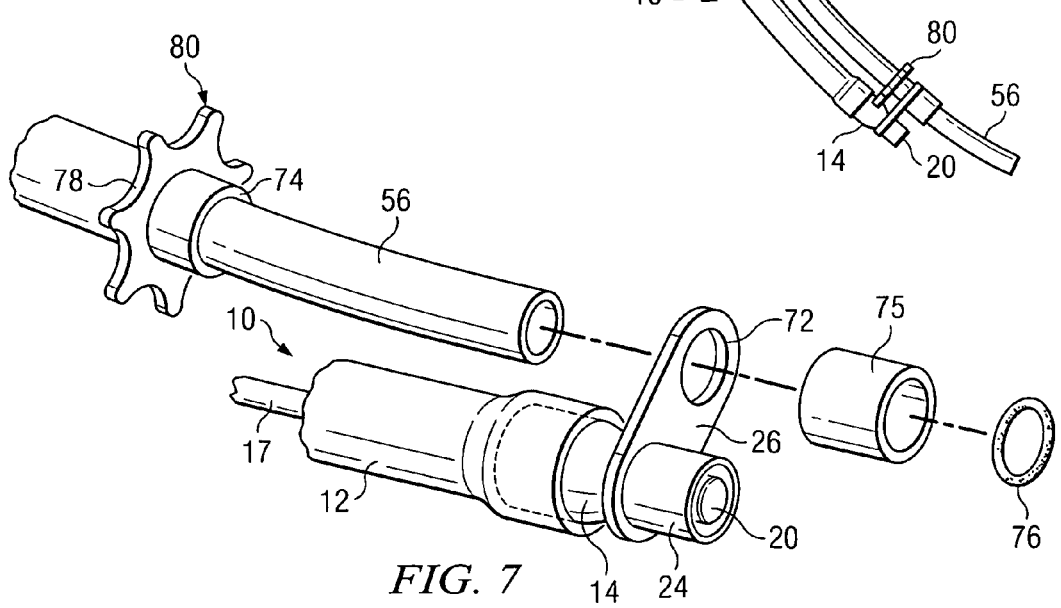
FIG. 7 is an isometric view of a portion of the surgical aspirator showing the manner in which the air shield is attached thereto.

FIG. 6 illustrates a preferred embodiment of the invention in which a surgical aspirator 54 comprising the instrument to which the air shield 10 is attached. The surgical aspirator device 54 is of conventional construction and of the type connected to a source of suction. The device 54 includes a suction tube 56 which can be placed adjacent the area of operation for removing liquids from the surgical site. The aspirator 54 includes a metal tubular connection 58 that is connected to a flexible suction tube 60. The aspirator 54 also includes a hand grip 62 connected to a rigid tubular member 64 which terminates with the suction tube 56 that is adapted for removing liquids via the suction forces. The liquid is removed via the suction action and transferred through the aspirator device 54, though the suction tubing 60, and collected in a container at the source of suction in a standard manner. The aspirator 54 is adapted to include a clamp 66 attached to the tubular member 64 of the aspirator 54. The clamp 66 includes a member 68 having a hole through which the air tube 12 is inserted to hold the air tube 12 next to the aspirator 54. The member 68 is fastened to the tubular part of the clamp 66 which is slid over the rigid tubular member 64 and held there by a short length of plastic tubing 67. Alternatively, the member 68 could have a C-shaped opening into which the air tube 12 can be pressed. The upper end of the aspirator 54 can also be equipped with another similar clamp (not shown) to attach the air tube 12 thereto at such location. With this arrangement, the surgeon or attendant can grasp the surgical aspirator 54 and at the same time grasp the air tube 12 with the same hand. The imager at the end of the air tube 12 is fastened adjacent the end of the suction tube 56. The operator can manipulate the aspirator device 54 to locate the lens 20 of the imager adjacent the surgical site so that an image can be captured and displayed on the video display 48. The details of the manner in which the imager and air shield 10 are attached to the suction tube 56 are illustrated in FIG. 7.

The air shield 10 is removably attached to the suction tube 56 portion of the dental aspirator 54. The bracket 26 is welded to the barrel 24 of the air shield 10. The bracket 26 is formed with a hole 72 therein. The hole 72 is of a diameter as to slip over the suction tube 56 of the aspirator 54. When the air shield 10 is attached to the aspirator 54, the bracket 70 is slipped over the suction tube 56 until abutted against the shoulder 74 of the suction tube 56. Then a short section of silicon tubing 75 is slid on the suction tube 56, followed by a small O-ring 76 which is stretched over the suction tube 56 and slid up against the silicon tube section 75. The bracket 70 thus holds the end of the air tube 12 and the imager against axial movement with respect to the aspirator 54. It can be seen in FIG. 7 that the air tube 12 is stretched over the back end of the tubular fitting 14. The air tube 12 is preferably constructed of silicon so that it can be sterilized in an autoclave. Indeed, all parts of the air shield 10 can be sterilized in an autoclave, except the camera 16, which can be sterilized with a suitable solution. Additionally, all parts of the air shield 10 can be sterilized during manufacture and be made such that it can be totally disposable.

Figure 8:
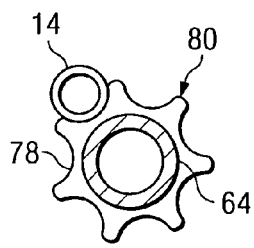
FIG. 8 is a cross-sectional view of the surgical aspirator showing the mechanism for adjustably fixing the air shield thereto at different angular locations.

During installation of the air shield 10 on the suction tube 56 of the aspirator 54, the tubular fitting 14 is nested in one of the notches of a notched ring 80 shown in FIG. 8. The notched ring 80 is fixed, such as by welding, to the surgical aspirator 54. With this arrangement, the air shield 10 can be adjustably fixed to a desired annular position around the suction tube 56. The attachment of the air tube 12 to the aspirator 54 using the clamp 68 maintains the fitting 14 nested within one of the notches 78. However, the fitting 14 can be easily rotated from one notch 78 to another notch of the notched ring 80 during the procedure to change the annular position of the air shield 10 around the suction tube 56. The annular position of the air shield 10 around the suction tube 56 can be changed during a procedure, depending on where it is desired to place the suction tube 56 with respect to the tissue being treated. It is realized that the lens 20 of the imager should preferably be placed at a position that best affords the surgeon the optimum view of the area of interest, and this position may change from time to time. The position of the imager can also be continuously changed by manipulating the orientation of the dental aspirator 54 by one hand of the surgeon, and using a scalpel or other surgical instrument with the other hand. The magnification of the image as captured by the camera 16 is accomplished by movement of the surgical aspirator 54 with respect to the area of interest.

The removal of the air shield 10 from the surgical aspirator 54 is easily accomplished by removing the O-ring 76 and the silicon tubular member 75 from the end of the suction tube 56 and sliding the bracket 70 of the imager off the suction tube 56. The air tube 12 can be pulled out of the clamp 68. The camera 16 and the attached cable 17 can be pulled out of the air tube 12 so that the components can be sterilized separately.

Figure 9:
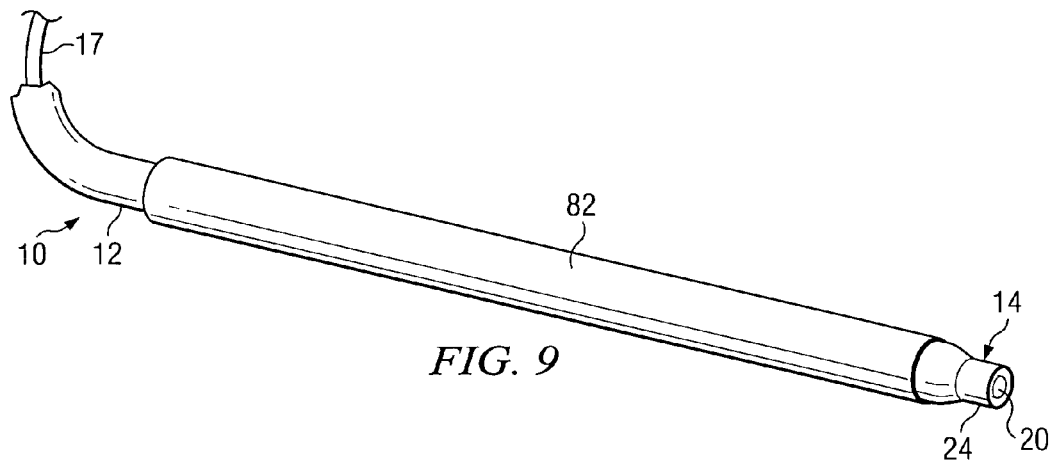
FIG. 9 illustrates another embodiment of the air shield having a stiffener that can be used as a handle in the event that the air shield is used by itself.

While it may be preferred to employ the air shield 10 with another instrument, such as the surgical aspirator 54 described above, this combined use is not necessary. Indeed, the air shield 10 can be used by itself. FIG. 9 illustrates the air shield 10 equipped with a stiff tubular handle 82 that is slipped over the air tube 12. The tubular handle 82 allows the user to grasp the air shield 10 and manipulate it to the desired position and hold it there despite the flexible nature of the air tube 12. The stiffener 82 can be integrated with the air tube 12 and attached thereto if desired. Alternatively, the handle 82 can be cross-sectionally C-shaped for forcing the flexible air tube 12 therein, and removed if desired.

Figure 10:
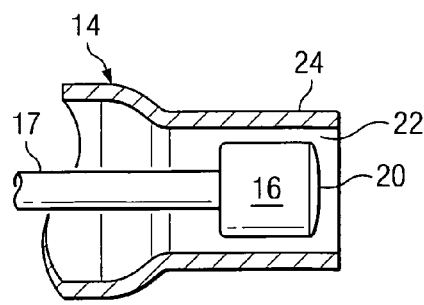
FIG. 10 is a cross sectional view of the barrel of the fitting and the annular orifice around the imager for allowing pressurized air to pass therethrough and form a protective envelope.

FIG. 10 is a cross-sectional view of the imager held within the barrel 24 of the tubular fitting 14. It can be seen that an annular orifice 22 is defined between the inside diameter of the barrel 24 of the fitting 14 and the camera 16. The annular orifice 22 is effective to allow pressurized air to pass therethrough and form an envelope around the lens 20 of the imager. While the camera 16 and the lens 20 of the imager are not fixed in a centered position within the barrel 24, the air flow therearound tends to center the imager therein so as to allow a circular flow of air therearound. Those skilled in the art may find it advantageous in certain circumstances to form plural webs or spacers around the imager to keep it centered within the barrel 24. It is noted in FIG. 10 that the body of the fitting 14 is larger than the barrel end 24. The body of the fitting 14 allows the end of the silicon air tube 12 to be slipped thereover and frictionally held in such position. The inside cylindrical surface of the fitting gradually decreases in diameter toward the barrel 24 to facilitate insertion of the camera 16 therein.

Figure 11:
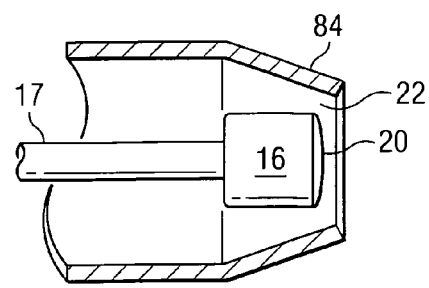
FIG. 11 illustrates another arrangement of an annular passage for pressurized air around the imager.

FIG. 11 illustrates another configuration of a barrel 84 according to the invention. Here, the barrel 84 is funnel-shaped and has a narrowed end in which the imager is positioned. Many other barrel configurations are possible and may be adapted for use with the air shield according to the invention. It may be found that the use of internal spiral grooves or fins can create a swirl or vortex of air that is well adapted for maintaining the optical input of the imager clear of debris.

Figure 12:
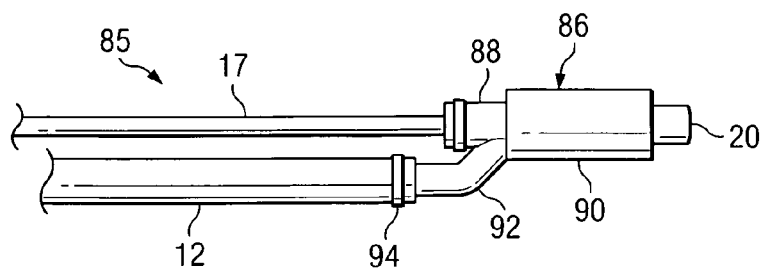
FIG. 12 is a side view of another embodiment of the air shield in which the camera extends outside the air tube.

While the preferred embodiment of the invention extends the camera 16 inside the air tube 12, this is not a necessary condition for the practice of the invention. To that end, FIG. 12 illustrates an embodiment of an air shield 85 in which the camera 16 and associated electrical cable 17 extends outside the air tube 12. Here, a termination fitting 86 is employed to bring together the air tube 12 and the camera 16 so that an air stream envelope is generated around the lens 20 of the imager. The termination fitting 86 includes an inlet sleeve 88 through which the camera 16 and cable 17 are routed. The sleeve 88 can be tightened and clamped around the camera cable 17 by a clamp or binder 88 of conventional design. The lens 20 of the imager is positioned in the exit opening of the termination fitting 86. While not shown, an annular orifice exists between the exit opening in the termination fitting 86 and the body of the imager adjacent the lens 20.

The termination fitting 86 includes a body portion 90 that encircles the camera 16 and is spaced therefrom. A tubular air inlet 92 is coupled to the body portion 90, and is connected to the air tube 12. The air tube 12 can be slipped over the tubular air inlet 92 and clamped with a clamp 94. The pressurized air that is carried by the air tube 12 is coupled inside the body 90 of the termination fitting 86, and is then coupled to the annular orifice around the imager, thereby generating the air envelope that prevents liquids and particulate matter from being splattered onto the lens 20 of the imager.

Figure 13:
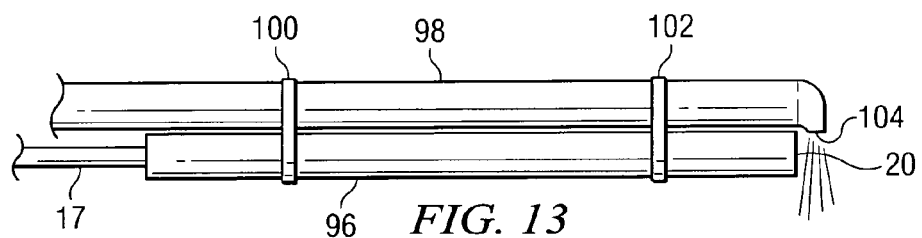
FIG. 13 is a drawing illustrating another embodiment of the air shield in which the airstream is directed laterally across the optical input of the imager.

With reference now to FIG. 13, there is illustrated another embodiment of the air shield of the invention in which the air stream is directed transverse to the line of sight of the imager. The camera 16 can be encased in a rigid cover 96. The optical input 20 of the imager captures an image that is generally located in front of the imager. An air tube 98 extends alongside the imager and can be fastened thereto by band-type fasteners 100 and 102. The end of the air tube 98 has a side opening 104 so that the stream of pressurized air is directed laterally across the lens or optical input 20 of the imager. With this arrangement, any debris initially directed toward the optical input 20 of the imager is redirected so that it does not contaminate the lens 20. The air stream that prevents debris from contaminating the optical input 20 of the imager can be directed at any other included angle between the transverse angle shown, and when the air stream is coincident and away from the line of sight of the imager as described above.

Figure 14:
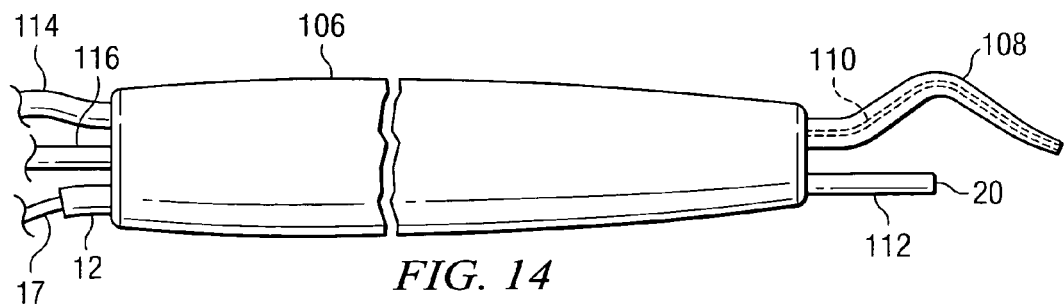
FIG. 14 is a drawing of another embodiment of the invention in which the air shield and imager are integrated into a device.

FIG. 14 illustrates the air shield of the invention integrated into a tool 106. The tool illustrated is an ultrasonic scaler 106 of the type having a tip 108 that is effective to remove plaque and other deposits from hard tooth tissues. The ultrasonic tip 108 is tubular and includes a water channel 110 formed therethrough. The composite air shield and imager 112 can be constructed and integrated with the other components of the ultrasonic scaler 106. The imager includes an optical input 20 that is surrounded by an air tube for directing an air stream in front of the optical input 20 to prevent debris from contaminating the optical input 20 of the imager. The electrical energy required of the ultrasonic scaler 106 is coupled thereto by the electrical input conductors 114. The water coupled to the channel 110 in the tip 108 is coupled to the ultrasonic scaler 106 by the liquid input connection 116. The air tube 12 with the camera cable 17 therein is coupled to the ultrasonic scaler 106 at the back end thereof, and through the scaler 106 to the front end at a location to capture images adjacent the end of the tip 108. In this manner, the surgeon or assistant can view the area (on a video screen) in which the ultrasonic scaling procedure is being conducted, and maintain the optical input 20 of the imager clean and free of debris, contaminants and particulate matter. While not shown, the ultrasonic scaler 106 can be constructed with a conduit therethrough from the back end to the front end. The composite air tube 12 and camera 16 can be routed through the conduit and slideable therein. A rotatable finger or thumb wheel (not shown) which frictionally engages the outer surface of the air tube 12 can be attached to the tool 106. When it is desired to move the composite air tube 12 and camera 16 to adjust the optical input closer or further away from the tip 108, the thumb wheel need only be rotated to accomplish such movement. Other telescopically movable mechanisms can be employed to move the camera 16 within the air tube 12.

FIG. 15 illustrates another surgical instrument to which the air shield of the invention can be removably attached. The instrument 120 comprises a Pritchard periosteal elevator having a planar elevator 122 at one end and a smaller blade 124 at the other end. The elevator 122 can be used to move the gingiva away from the tooth or bone and carry out surgical procedures. Attached to the instrument 120 is an air shield 126 constructed according to the invention. The air shield 126 of this embodiment is constructed with a rigid tubular member 128 to which a pair of spring-like clips 130 and 132 are welded. The clips 130 and 132 are C-shaped and adapted for clamping around the body of the instrument 120. The end of the tubular member includes a fitting 138 for receiving a video camera (not shown) therein, in the manner described above. The video camera is attached to an electrical conductor 17 for carrying video signals to the image processing equipment. Attached by a connector 127 to the other end of the rigid tubular member 128 is a flexible air tube 12. The electrical cable 17 extends through the air tube 12 and the rigid tubular member 128 to the fitting 138 attached at the frontal end of the tubular member 128. With this arrangement, the site at which the procedure is being carried out by the blade 124 is both illuminated and imaged by the video camera. Importantly, the lens or optical input of the camera is maintained clear of debris and residue generated during the procedure. When it is desired to conduct a surgical procedure with the elevator 122, the air shield 126 can be removed from the instrument via the clips 130 and 132 and reversed so that the fitting 138 in which the camera is housed, is directed toward the elevator 122.

In operation of the air shield of the invention, it is manipulated so as to be located sufficiently close to the procedure being carried out, preferably, but not exclusively, a surgical procedure in which body fluids and/or tissue particles are present. In this instance, there is a high likelihood that such body fluids and tissue particles will be projected toward the lens of the imager and obscure viewing of the procedure. Since a gas is the mechanism for providing a continuous shield to deflect the body fluids and tissue particles, the body fluids and tissue particles are deflected and do not come into contact with the lens of the imager. Air or another suitable gas is preferable, since such medium does not interfere with the imaging of the procedure, even if the air flow is turbulent. This contrasts with a liquid medium which can distort the captured image especially if the liquid includes turbulent flow. In addition, the use of a gas medium does not require removal thereof, as does a liquid medium. Indeed, if a liquid is used to clean the lens of an imager, then the liquid must eventually be suctioned, which is frequently required in order to maintain the surgical site free of excess liquids. A water or liquid lens cleaner is much more difficult to remove, as a liquid always seeks the lowest level in the cavity, which must be accessible to remove the liquid therein, usually by suction means. An air medium, on the other hand, can easily escape from any opening in the cavity to the atmosphere, and does not require any additional equipment to facilitate the escape of the spent air from the envelope. The supply of a clean gas is more readily available than a supply of a clean liquid. Moreover, liquids used for medical lavage purposes require storage, whereas a supply of a gas for maintaining the lens of an imager clean can very often be obtained from the atmosphere of the room, and filtered to render it sufficiently clean and pure for use in medical and dental procedures. Importantly, the use of the air shield of the invention prevents the lens of an imager from being contaminated with body fluids and tissue particles. This contrasts, with other imager cleaning techniques using water or liquids, where the lens is generally not prevented from being contaminated, but rather once it is, the liquid is used to purge the lens of contaminants.

The air shield of the invention can be integrated with a number of different medical and dental instruments, or attached thereto. The attachment of the air shield to instruments can be accomplished in a convenient manner. For example, a dental air-operated drill can be easily equipped with the air shield of the invention. The air shield and the optical imager can be attached to the drill by plastic or metal clamps, and both the drill and the air shield can share the same source of pressurized air. The imager can be focused on the drilling area so that the doctor can view an enlarged image of the same on a video display, while the air shield maintains the optical input of the imager clear of obscuring material. Because of its elongate nature, the air shield and imager can be attached to a host of other instruments, both medical and otherwise. Indeed, the air shield and imager of the invention can be used with industrial equipment and mechanical tools and sensor systems utilized in environments where adverse conditions exist that would otherwise cause the lens of the optical equipment to become contaminated.

From the foregoing, it is noted that the preferred embodiment of the invention employs the air shield and associated imager in association with a hand-held surgical device. However, the use of the invention with another device is not necessary to the practice of the invention. Indeed, the air shield itself with the endoscopic imager can be used alone, such as in applications where it is desired to simply observe various areas or tissues of the body, without corresponding surgical treatment. For example, the air shield and imager can be used as a larynxscope to view the larynx or esophagus of a person for purposes of diagnosis. The air shield and associated imager can thereafter be attached to other instruments and inserted in a person's throat to obtain tissue samples and conduct surgical treatments, while at the same time viewing the procedure via the imager on a video display.

The preferred embodiment employs a camera in the exit opening of a tube carrying pressurized air. As noted above, other optical apparatus can be utilized, including a fiber optic bundle where it is desired to maintain the optical input thereof clear of contaminants. In addition, the preferred embodiment employs an annular orifice to produce a circular envelope of air around the imager. Other orifice arrangements can be utilized, including a number of spaced-apart individual orifices to form the envelope of an air stream that provides a protective air shield around the optical input of the imager.

While the preferred and other embodiments of the invention have been disclosed with reference to specific air shields, and associated methods of operation thereof, it is to be understood that many changes in detail may be made as a matter of engineering choices without departing from the spirit and scope of the invention, as defined by the appended claims.

What is claimed is:

1. A method of maintaining an imager clear of debris during a procedure on a body tissue where the debris would otherwise obscure an optical input of the imager, comprising: using a pressurized gas to form an annular envelope of a stream of the pressurized gas; embedding the optical input of the imager in the annular envelope of gas so that the optical input of said imager is surrounded with the annular envelope of gas, directing the annular gas stream downstream from the optical input, without the use of a deflector apparatus that deflects the gas stream toward the optical input of said imager, to form an annular gas shield around the optical input of said imager so that the debris initially directed from any angle toward the optical input is redirected by the annular gas shield away from the optical input, said pressurized annular envelope of gas directed downstream from the optical input forming a turbulent flow of gas directly in front of the optical input to thereby remove liquids that collect on the optical input of said imager, whereby debris is prevented from accumulating on the optical input of the imager, and preventing movement of apparatus in the annular envelope of the pressurized gas at a location that spoils the annular envelope of gas and obstructs viewing through the imager to thereby provide an uninterrupted annular gas shield and thus uninterrupted shielding of debris generated by the procedure from obscuring the optical input of said imager.

2. The method of claim 1, further including maintaining a continuous annular envelope of the gas stream directed axially away from the optical input during the tissue procedure in which the imager is used.

3. The method of claim 1, further including placing the imager in an end of a gas tube in which pressurized gas exits therefrom, so that an annular orifice is formed between the optical input of the imager and the gas tube.

4. The method of claim 3, further including using a camera and associated electrical cable for carrying images, and inserting the camera and associated electrical cable in the gas tube.

5. The method of claim 4, further including sliding the camera axially in said gas tube to adjust a size of an image captured by the camera.

6. The method of claim 1, further including encircling the optical input of the imager with a tubular member through which a pressurized gas is passed, and forming the gas stream circumferentially around the imager to form the annular envelope of gas and deflect debris directed to the optical input of the imager.

7. The method of claim 6, wherein said tubular member defines a gas tube, and further including fastening said gas tube to a tool used in a surgical procedure.

8. The method of claim 1, further including forming an annular flow of gas adjacent the front of said optical input and directed axially outwardly therefrom to remove droplets of liquid therefrom.

9. The method of claim 1, further including moving said imager axially in said gas tube to adjust an efficiency in which debris is deflected from the optical input of the imager.

10. The method of claim 1, further including allowing the gas to escape from an end of the imager to the atmosphere.

11. A method of maintaining an imager clear of debris that can obscure an optical input of the imager, comprising:
    passing a pressurized gas downstream and circumferentially around the optical input of the imager to form an annular envelope of gas that circumscribes the optical input, and to form an inner volume of said annular envelope of gas characterized by an inner turbulent flow of the gas in front of the optical input of said imager for removing droplets of liquid from the optical input;

redirecting debris initially directed toward the optical input from any position in front of the optical input, away from the optical input using a force of the annular envelope of said gas;

forming the annular envelope of gas around the optical input of the imager without the use of deflector apparatus that deflects the gas stream across a face of the optical input of said imager; and allowing the gas to escape to the atmosphere.

12. The method of claim 11, further including placing the imager inside a tube carrying the gas so that the annular envelope of gas escapes around the imager and axially outwardly from the optical input.

13. The method of claim 11, further including integrating the imager with a tube carrying the pressurized gas into a gas shield device, and attaching said gas shield device to a medical or dental instrument.

14. The method of claim 13, further including removably attaching said gas shield device to said medical or dental instrument.

15. A gas shield for maintaining an imager clear of debris that can obscure an optical input of the imager, comprising;

a tubular member for carrying a pressurized gas, said tubular member having a first end receiving pressurized gas from a source, and said tubular member having a second end;

at least one conductor carrying signals representative of an image captured by said imager, said conductor extended through said tubular member to said imager;

the optical input of said imager adapted to be exposed in an environment of debris during a tissue procedure, said optical input located adjacent the second end of said tubular member so that the pressurized gas carried by said tubular member passes downstream annularly around the optical input of said fiber optic conductor and generates an annular envelope of a gas stream around the optical input to thereby shield the optical input from debris and redirect the debris away from the optical input of said imager, and said gas shield does not include gas stream deflection apparatus to deflect the direction of flow of said gas stream at a right angle toward the optical input of said imager; and said gas shield does not include apparatus in the annular envelope of the pressurized gas to spoil the annular envelope of gas to thereby provide an uninterrupted annular gas shield and thus uninterrupted shielding of debris generated by the tissue procedure from obscuring the optical input of said imager.

16. The gas shield of claim 15, further including a clamp for clamping the imager against movement within said tubular member.

17. The gas shield of claim 16, further including means for adjusting the imager to a desired axial location within said tubular member, and then clamping the imager against axial movement within said tubular member.

18. The gas shield of claim 15, wherein said tubular member is connected to a flexible air tube, and said conductor is extended through said air tube.

19. The gas shield of claim 15, further including a device to which said gas shield is attached, and further including means for fastening the second end of said tubular member to different annular locations around said device.

* * * * *